United States Patent [19]

Ishiyama et al.

[11] 4,028,184
[45] June 7, 1977

[54] PROCESS FOR PRODUCING 3′,5′-CYCLIC ADENYLIC ACID

[75] Inventors: Jiro Ishiyama; Motohiko Kato, both of Noda; Fumihiko Yoshida, Matsudo; Tamotsu Yokotsuka, Nagareyama, all of Japan

[73] Assignee: Kikkoman Shoyu Co., Ltd., Noda, Japan

[22] Filed: Apr. 2, 1976

[21] Appl. No.: 673,067

Related U.S. Application Data

[63] Continuation-in-part of Ser. No. 592,061, June 30, 1975, abandoned, which is a continuation of Ser. No. 405,897, Oct. 12, 1973, abandoned.

[30] Foreign Application Priority Data

Oct. 16, 1972  Japan .......................... 47-102780

[52] U.S. Cl. ............................................. 195/28 N
[51] Int. Cl.$^2$ ......................................... C12D 13/06
[58] Field of Search ................... 195/28 N, 96, 112

[56] References Cited

UNITED STATES PATENTS 3,630,842  12/1971  Ishiyama et al. ................ 195/28 N
3,816,251  6/1974  Nakayama et al. .............. 195/28 N

*Primary Examiner*—R. B. Penland
*Attorney, Agent, or Firm*—Schuyler, Birch, Swindler, McKie & Beckett

[57] ABSTRACT

A process for producing 3′,5′-cyclic adenylic acid in a high yield at a lower price by culturing a strain belonging to the genus selected from the group consisting of Corynebacterium, Arthrobacter and Microbacterium such as, for example, *Corynebacterium murisepticum* No. 7-10 (ATCC 21977), Arthrobacter 11-211 (ATCC 21978) Microbacterium No. 205-CM7 (ATCC 21979), Microbacterium No. 205-CM-XA3 (ATCC 21980), or Microbacterium No. 205-MP-197 (ATCC 21976) in a medium containing nutrient sources such as, carbon sources, nitrogen sources, inorganic salts and the like but containing no precursors and having a pH of 5-9 at a temperature of 20°-40° C under aerobic condition. The obtained 3′,5′-cyclic adenylic acid is well-known for its participation in various biochemical reactions in vivo and for its active role as a mediator to various hormones. It has therefore always been highly evaluated biochemical reagent.

9 Claims, No Drawings

PROCESS FOR PRODUCING 3',5'-CYCLIC ADENYLIC ACID

CROSS REFERENCE TO THE RELATED APPLICATION

This application is a continuation-in-part of copending application Ser. No. 592,061 filed June 30, 1975, which is a continuation of abandoned application Ser. No. 405,897, filed Oct. 12, 1973, the disclosures of which are incorporated by reference.

The present invention relates to a process for producing 3',5'-cyclic adenylic acid by culturing microorganisms.

It has been well-known that 3',5'-cyclic adenylic acid participates in various biochemical reactions in vivo and that it plays an active part as a mediator for various hormones. It has therefore been highly evaluated biochemical reagent.

As a process for producing 3',5'-cyclic adenylic acid (hereinafter referred to as CAMP), the present inventors or some of them have established processes for producing CAMP by culturing a microorganism belonging to the genus selected from the group consisting of Corynebacterium, Arthrobacter or Microbacterium and having a capability of producing CAMP from a precursor such as, for example, adenine, hypoxanthine, succinyl adenine, 5-amino-4-imidazole-carboxamide, 7-amino-pyrazolo-(4,3-d)-pyrimidine, pyrazolo-(4,3-d)-pyrimidine, 4-amino-pyrrolo-(2,3d)-pyrimidine, pyrrolo-(2,3-d)-pyrimidine, a riboside containing one of said compounds as a base (Adenosine, inosine, succinyladenosine, 5-amino-4-imidazole-carboxamideriboside, 7-amino-3-($\beta$-D-ribofuranosyl)-pyrazolo-(4,3-d)-pyrimidine (Formycin A), 3-($\beta$-D-ribofuranosyl)-pyrazolo-(4,3-d)-pyrimidine (Formycin B), 4-amino-3-($\beta$-D-ribofuranosyl)-pyrro-(2,3-d)-pyrimidine (Tubercidin), 3-($\beta$-D-ribofuranosyl)-pyrro-(2,3-d)-pyrimidine (6-deaminoturbercidin), or a monoucleotide thereof (2'(3' or 5')-adenylic acid, 2'(3' or 5')-inosinic acid, 2'(3' or 5')-succinyladenylic acid, 5-amino-4-imidazolecarboxamideribose-2'(3' or 5')-phosphate, Formycin A-2'(3' or 5')-monophosphate, Formycin B-2'(3' or 5')-monophosphate, Tubercidin-2'(3' or 5')-monophosphate, 6-deaminotubercidin-2'(3' or 5')-monophosphate or the like) in a medium containing the foregoing precursor (See, for example, U.S. Pat. No. 3,630,842, Japanese patent publication No. 33/72, Japanese patent publication No. 34/72, Japanese patent publication No. 1,838/72, Japanese patent publication No. 1,839/72 and the like.). CAMP can be produced at an extremely lower price with a great easiness by those processes as compared with the conventional ones by chemical synthesis, however, those processes are not always satisfactory ones since it is required to add a large amount of the foregoing compounds in the culture medium.

Further, in U.S. Pat. No. 3,816,251, it is described that CAMP is produced by culturing a CAMP-producing strain in a medium wherein fluoride is added with or without adding a precursor such as adenine, adenosine and the like. However, the CAMP-producing strains used in the method of U.S. Pat. No. 3,816,251 are those which produce CAMP either in the presence of a precursor or by addition of fluoride to the medium when no precursor is added. Accordingly, the addition of fluoride to the medium is essential to the method of U.S. Pat. No. 3,816,251 but not essential to the method of the present invention.

The present inventors have isolated, as a result of studying intensively on a process for producing CAMP at a lower price with a great easiness using microorganisms, a large number of mutants capable of producing CAMP, when cultured in a medium containing no foregoing precursors and no fluoride, that is, in an ordinary nutrient medium, by subjecting a microorganism capable of producing CAMP from the foregoing precursors such as, for example, Corynebacterium murisepticum No. 7 (ATCC 21374, FERM-P No. 206), Arthrobacter 11 (ATCC 21375, FERM-P No. 207), Microbacterium No. 205 (ATCC 21376, FERM-P No. 106); the abbreviation "ATCC" stands for the access number registered by American Type Culture Collection, 12301 Parklawn Drive, Rockville Md, U.S.A., a public depository of U.S.A. and the abbreviation "FERM-P" stands for the access number registered by Fermentation Research Institute, Agency of Industrial Science and Technology, 5 chome 8-1, Inage, Chiba, Japan, a public depository of Japan) or the like to treatment for artificial mutation and completed the present invention.

An object of the present invention is to provide a process for producing CAMP by culturing a microorganism capable of producing CAMP in a medium containing no precursor.

Another object of the present invention is to provide a process for producing CAMP at a lower price with a great easiness compared with the conventional process.

Still another object of the present invention is to provide a microorganism capable of producing CAMP in a medium containing no foregoing precursors and no fluoride.

Other objects will become apparent from the following description.

The present invention is concerned with a process for producing CAMP which is characterized by culturing in a medium containing nutrient sources such as carbon sources, nitrogen sources, inorganic salts and the like a microorganism belonging to the genus selected from the group consisting of Corynebacterium, Arthrobacter and Microbacterium and having a capability of producing CAMP in a medium containing no procursor such as, for example, adenine, hypoxanthine succinyladenine, 5-amino-4-imidazolecarboxamide, 7-amino-pyrazolo-(4,3-d)-pyrimidine, pyrazolo-(4,3-d)-pyrimidine, 4-amino-pyrrolo-(4,3-d)-pyrimidine, pyrrolo-(2,3-d)-pyrimidine, a riboside containing one of the said compounds as a base or a monoribonucleotide thereof and no fluoride to produce CAMP, collecting produced CAMP from the culture broth. According to the present process, CAMP can be produced at a lower price with a great easiness compared with the conventional one.

The invention will be illustrated in greater detail in the following description.

Any of microorganisms may be employed in the present process if it belongs to the genus selected from the group consisting of Corynebacterium, Arthrobacter and Microbacterium and has a capability of producing CAMP when cultured in a medium containing assimilable carbon source, nitrogen source, inorganic salts and the like in a sufficient quantity, but containing as a precursor no adenine, hypoxanthine, succinyladinine, 5-amino-4-imidazolecarboxamide, 7-amino-pyrrazolo-(4,3-d)-pyrimidine, pyrazolo-(4,3-d)-pyrimidine, 4- amino-pyrro-(2,3-d)-pyrimidine, pyrrolo-(2,3-d)-pyrimidine, a riboside containing as a base one of the above-mentioned compounds, a monoribonucleotide thereof or the like and no fluoride.

In the present invention, the capability of producing CAMP means a capability of producing CAMP in proportion of 0.3 mg/ml or more.

Typical of these are, as a microorganism belonging to Corynebacterium, artificial mutants of Corynebacterium murisepticum No. 7 (ATCC 21374, FERM-P No. 206) such as for example, Cornyebacterium murisepticum No. 7-10 (ATCC 21977, FERM-P No. 1555) or the like, as one belonging to Arthrobacter, artificial mutants of Arthrobacter 11 (ATCC 21375, FERM-P No. 207) such as, for example, Arthrobacter 11-211 (ATCC 21978, FERM-P No. 1556) or the like, as one belonging to Microbacterium, artificial mutants of Microbacterium No. 205 (ATCC 21376, FERM-P No. 106) such as, for example, Microbacterium No. 205-CM7 (ATCC 21979, FERM-P No. 1557), Micro bacterium No. 205-CM-XA3 (ATCC 21980, FERM-P No. 1558), Microbacterium No. 205-MP-197 (ATCC 21976, FERM-P No. 2449) or the like.

To obtain artificial mutants from the above-mentioned parent strains, the ordinary treatment for artificial mutation may be used effectively. For example, the parent strains are subjected to irradiation by x-rays, ultraviolet light or the like, treatment by a chemical mutagenic agent such as, for example, nitrosoguanidine, diethyl sulfate, methylethyl sulfate, $NaNO_2$, acridine, nitrogen mustard or the like. The thus obtained mutants are screened in the ordinary manner and then mutants having a capability of producing CAMP without adding the foregoing precursors in the absence of fluoride are isolated.

A technique for preparing artificial mutants which produce a mixture of purine derivatives among which is 5′ adenylic acid is described in U.S. Pat. No. 3,298,923. An example of treatments for mutation whereby a mutant strain employable for the present process may be obtained, the following method is given.

To a 10 ml (Number of cells: $2 - 5 \times 10^9$/ml) of cell suspension of Corynebacterium murisepticum No. 7 (ATCC 21374, FERM-P No. 206), Arthrobacter 11 (ATCC 21375, FERM-P No. 207) or Microbacterium No. 205 (ATCC 21376, FERM-P No. 106) at the logarithmic growth phase is added 0.1 ml of diethyl sulfate and the mixture is kept at 30° C for 60 minutes with shaking to contact well. The resultant is smeared onto an agar plate medium (Note 1) and cultured at 30° C for 48–100 hours. The appeared colonies are picked up at random, inoculated in an agar slant medium (Note 2) and cultured at 30° C for 48–100 hours. Thereafter, the thus cultured microorganism is inoculated in 3 ml of a liquid culture medium (Note 3) in a test tube (diameter: 2 cm, length: 15 cm) and cultured at 30° C for 24 hours with shaking at 289 r.p.m. The accumulation of CAMP in the cultured broth is checked by a paper chromatography.

The method for quantitative determination of CAMP by means of paper chromatography is as follows:

First of all, 10 μl of the culture liquer is placed at one end of a filter paper (40 × 40 cm in size) and the wet spot is allowed to dry in air, and then subjected to a two-dimentional paper chromatography using the following developing agents:

First developing agent:

Iso-butylic acid : 1N-acetic acid :1N-$NH_4OH$ (10 : 1 : 5 by volume)

Second developing agent:

Saturated $(NH_4)_2SO_4$ : 1M. sodium acetate: isopropanol (80 : 20 : 2 by volume)

The resulting paper is dried in air and the portion corresponding to CAMP (a spot showing the same ultraviolet absorption as the $R_f$ value of a pure CAMP) is cut therefrom and subjected to extraction with water at 100° C for 30 minutes. The resulting solution is subjected to spectro analysis by means of spectro photometer thereby to determine the ultraviolet absorption value (O.D. value) at 258 mμ. The resulting O.D. value is divided by Molecular extinction coefficient ($\epsilon =$ 14650) [see M. Smith, G. Drummond and H. G. Khorana, J.A.C.S. 83, 698 (1961)] and then multiplied by the molecular weight of CAMP (329.2) whereby the amount of CAMP is calculated.

Second, the confirmation experiment is carried out as to the strains capable of producing 0.3 mg/ml or more of CAMP according to the following manner: The cultivation is carried out in the same manner as above using the same culture medium as used in the screening method in a further larger scale, (such as for example, using 1 l of culture medium), and the resulting culture liquor is subjected to purification treatment in the same manner as shown in Example 1 described hereinafter, and the resulting crystal is subjected to IR, NMR and Mass spectrometry in comparison with a pure CAMP-crystal thereby to confirm it as being CAMP.

Note 1:

A medium composed of 1% of glucose, 0.5% of $(NH_4)_2SO_4$, 0.5% of urea, 1% of $KH_2PO_4$, 1% of $K_2HPO_4$, 0.3% of casamino acid, 30 γ/l of biotin, 1% of $MgSO_4 \cdot 7H_2O$, 2% of agar and of pH 7.0; and sterilized at a pressure of 15 lb. per sq. in for 10 minutes.

Note 2:

A medium composed of 1% of beef extract, 1% of polypeptone, 0.5% of yeast extract, 0.3% of NaCl and 2% of agar and of pH 7.0; and sterilized at a pressure of 15 lb. per sq. in. for 15 minutes.

Note 3:

A medium composed of 0.01% of $ZnSO_4 \cdot 7H_2O$, 0.5% of urea, 0.5% of $(NH_4)_2SO_4$, 1% of $KH_2PO_4$, 1% of $K_2HPO_4$, 0.5% of arginine, 30 ε/l of biotin, 5% of glucose, 1% of $MgSO_4 \cdot 7H_2O$ and sterilized at a pressure of 15 lb. per sq. in. for 12 minutes.

The percent showing the rate of each ingredient in the above-mentioned medium is given in a figure divided the weight of the ingredient by the volume of the medium, that is, the term "percent" denotes the weight of the ingredient in 100 ml of the medium. The same expression is used herein after unless otherwise noted.

Table 1 is given to compare the productivity of CAMP and nutritional requirements between the parent strain and one of the thus obtained mutants having a capability of producing CAMP without adding the foregoing precursor and fluoride to the medium.

Table 1

| Strain | Productivity of CAMP* | Vitamine requirements | Amino acid requirements |
|---|---|---|---|
| Corynebacterium murisepticum No. 7 (Parent) | none | Biotin | Amino acid is not particularly required, however, asparagine, aspartic acid and arginine promote the growth of the |

Table 1-continued

| Strain | Productivity of CAMP* | Vitamine requirements | Amino acid requirements |
|---|---|---|---|
| | | | bacteria |
| Arthrobacter 11 (Parent) | " | " | " |
| Microbacterium No. 205 (Parent) | " | " | " |
| Corynebacterium murisepticum No. 7 – 10 (Mutant) | 0.3 mg/ml | " | " |
| Arthrobacter 11-211 (Mutant) | 0.4 mg/ml | " | " |
| Microbacterium No. 205-CM7 (Mutant) | 0.7 mg/ml | " | " |

*The shaking culture was carried out by using a medium (Note 3) at 30° C for 24 hours with 289 r.p.m.

As shown in Table 1, said mutants show no particular nutritional requirements compared with their parent strains and are capable of producing CAMP without addition of the foregoing precursors and fluorides.

Naturally, mutants being different in nutritional requirements from their parent strains may be used in the process by satisfying their nutritional requirements if they are capable of producing CAMP without addition of said precursors and fluorides.

For example, the present inventors have isolated xanthine requiring mutant Microbacterium No. 205-CM-XA3 (ATCC 21980, FERM-P No. 1558) by subjecting Microbacterium No. 205-CM7 (ATCC 21979, FERM-P No. 1557) to nitrosoguanidine treatment as shown in the following.

To a cell suspension of Microbacterium No. 205-CM7 at the logarithmic growth phase (number of cells: ca $10^9$/ml: a phosphate buffer solution of pH (6.5) is added nitrosoguanidine so as to make its final concentration 0.1 mg/ml and the cells are contacted to the chemical for 30 minutes at 0° C and are collected by centrifugation. Thereafter, the collected cells are cultured at 30° C with shaking for 16 hours in a medium (Note 4) and then the resultant cells are collected again. After the collected cells are washed by a phosphate buffer solution (pH 7.0), the washed cells are suspended in a medium (Note 5) so as to make the number of cells $1 - 5 \times 10^7$/ml and penicillin is added at the rate of 2000 units per ml. Thereafter, the microorganism is cultured with standing for 16 hours at 30° C. Subsequently, the cells are collected and washed with a phosphate buffer solution (pH 7.0). The washed cells are smeared in the same medium as described in Note 4 except that 2% of agar are added thereto and cultured for 72 hours at 30° C. From the appeared colonies, strains capable of growing in the same medium as described in Note 4 except that 2% of agar are added thereto, but incapable of growing in the same medium as described in Note 5 except that 2% of agar are added thereto are isolated according to replica method. Follwing that, the strains are inoculated in the same medium as described in Note 3 except that 100 γ/ml of xanthine are added thereto and cultured with shaking for 48 hours at 30° C. Thereafter, the accumulation of CAMP is checked and one of the isolated strains capable of producing CAMP is called as Microbacterium No. 205-CM-XA3.

Note 4:

A medium composed of 20 mg/l of xanthine, 5% of glucose, 0.2% of $(HN_4)_2SO_4$, 0.5% of $KH_2PO_4$, 0.5% of $K_2HPO_4$, 0.2% of vitamin-free casamino acid, 30 γ/l of biotin, 0.05% of $MgSO_4.7H_2O$ and of pH 7.0 (adjusted with 3N—KOH aqueous solution); and sterilized at a pressure of 15 lb. per sq. in. for 12 minutes.

Note 5:

A medium composed of 0.5% of glucose, 0.2% of $(NH_4)_2SO_4$, 0.5% of $KH_2PO_4$, 0.5% of $K_2HPO_4$, 0.2% of vitamin-free casamino acid, 30 γ/l of biotin, 0.05% of $MgSO_4.7H_2O$ and of pH 7.0 (adjusted with 3N—KOH aqueous solution); sterilized at a pressure of 15 lb. per sq. in. for 12 minutes.

When cultured with shaking the thus obtained Microbacterium No. 205-CM-XA3 and its parent strain, Microbacterium No. 205-CM7 for 48 hours at 30° C in a medium Note 6 wherein the added amount of xanthine has been adjusted, as shown in Table 2, the CAMP productivity of Microbacterium No. 205-CM-XA3 increased to a great extent, compared with that of the parent strain.

Note 6:

The same medium as described in Note 3 except that xanthine is added thereto so as to make its concentration 100 γ/ml.

Table 2

| Strain | Productivity of CAMP | Colour of colony | Nutritional requirements |
|---|---|---|---|
| Microbacterium No. 205-CM7 | 0.6 mg/ml | yellow* | biotin |
| Microbacterium No. 205-CM-XA3 | 1.8 mg/ml | white | biotin and xanthine |

*The colour of the colony is yellow, but it changes to white by natural mutation. The CAMP productivity thereof, however, does not change.

Furthermore, a mutant being resistant to a chemical reagent and capable of producing CAMP without addition of said precursors and fluorides may be also used as a microorganism in the present process. For example, to a cell suspension (Number of cells: ca $10^9$/ml, a phosphate buffer of pH 6.5) of Microbacterium No. 205 (ATCC 21376, FERM-P No. 106) at logarithmic growth phase is added nitrosoguanidine so as to make its final concentration 0.1 mg/ml and the mixtures are kept at 0° C for 30 minutes to contact well. The cells are then collected by centrifugation and the collected cells are smeared to the same medium as described in Note 1 except that 100 γ/ml of 6-mercaptopurine are added thereto to incubate at 30° C for 48 hours. The colonies which appear are transferred to the same slant culture medium as described as Note 2 except that 100 γ/ml of 6-mercaptopurine are added thereto to incubate at 30° C for 40 hours. One loopful of the growth is inoculated in 3 ml each of the same liquid medium as described in Note 3 in a test tube (diameter: 2 cm, length: 15 cm) and cultured at 30° C for 24 hours with shaking at the rate of 289 r.p.m. The accumulation of CAMP in the cultured broth is checked by a paper chromatography and a large number of strains having a high CAMP productivity are isolated. Among those strains, one strain is called Microbacterium No. 205-MP-197 (ATCC 21976, FERM-P No. 2449). Table 3 is given to compare the productivity of CAMP, resistance to 6-mercaptopurine and color of colony between the parent strain and thus obtained mutant.

Table 3

| Strain | Resistance to 6-mercapto-purine (100 γ/ml) | CAMP productivity* | Colour of colony |
|---|---|---|---|
| Microbacterium No. 205 (Parent) | does not grow | none | yellow |
| Microbacterium No. 205-MP-197 (Mutant) | grows | 3.5 mg/ml | white |

*The shaking culture was carried out by using a medium (Note 3) at 30° C for 24 hours with 289 r.p.m.

The vitamin and amino acid requirements of the mutant is the same as those of the present strain.

A part of the characteristics of these mutants is the same as stated before, however, the rest of the characteristics is not different from those of the parent strains, Corynebacterium murisepticum No. 7 (ATCC 21374, FERM-P No. 206), Arthrobacter 11 (ATCC 21375, FERM-P No. 207) and Microbacterium No. 205 (ATCC 21376, FERM-P No. 106) and the characteristics of those parent strains are described, for example, in U.S. Pat. No. 3,630,842 in detail.

Further, one of the methods for screening a strain which can be used in the present invention from non-mutants, that is, wild strains is as follows:

The strain is inoculated into 3 ml of a liquid medium placed in a test tube (2 cm × 15 cm), which medium has been prepared in advance by adding 10 ml of a solution containing a mixture of vitamins (thiamino 50 mg, riboflavine 50 mg, pyridoxine 50 mg, Ca-pantothate 50 mg, nicotinic acid 10 mg, paraaminobenzoic acid 10 mg, folic acid 10 mg, xanthine 100 mg and guanine 100 mg/100 ml of said solution) to 1000 ml of the same medium as that of above-mentioned Note 1 except that no agar is added, and subjected to shake culture at 25°–37° C, with 289 r.p.m. for 24–120 hours. The culture liquor is subjected to centrifugal separation. Ten ml of the resulting supernatant is placed at one end of a filter paper (40 × 40 cm in size) and the CAMP-productivity is determined by means of paper chromatography in the same manner as mentioned above, and strains capable of producing CAMP is determined to be a strain which can be used in the present invention. This screening method, of course, may be applied to mutants, too.

According to the present process, CAMP can be produced by inoculating the strain capable of being employed in the present process in a medium containing carbon and nitrogen sources assimilable to said strain, inorganic phosphates, inorganic salts other than phosphates if necessary and other components in an appropriate amount and culturing until the accumation of CAMP goes up to the maximum. It is preferred to culture at a pH of 5–9 for 24–80 hours at a temperature of 20°–40° C.

By way of example, the carbon source used in the medium can be a saccharine material such as, for example, glucose, starch hydrolysates, molasses, distillers' soluble, glycerine and the like; and alcohol such as, for example, inositol, mannitol, sorbitol, ribitol and the like; an organic acid such as, for example, fumaric acid, succinic acid, malic acid and the like; hydrocarbons such as, for example, n-paraffin, kerosene and the like, and the nitrogen source can be ammonium sulfate, ammonium chloride, urea, various amino acids, hydrolysate of amino acid high polymers, meat extract, corn steep liquor, rice bran, organism extracts such as fish soluble and yeast extract and the like. The inorganic phosphate can be potassium or sodium dihydrogen phosphate, dipotassium or disodium hydrogen phosphate, ammonium phosphate and the like. The inorganic salts except phosphates can be added to the medium and illustrative of these are magnesium sulfate, magnesium chloride, ferrous or ferric sulfate, ferrous or ferric chloride, zinc sulfate, cobalt sulfate, boric acid, a salt thereof such as potassium borate or sodium borate, fluoride such as potassium fluoride or sodium fluoride, manganese sulfate, manganese chloride and the like. Although fluoride may be added to the medium, it is not a necessary addition since CAMP will be accumulated absent the presence of fluoride. In addition to these, the addition of microelements in favorable and typical of these are Vitamins, such as for example, biotin, Vitamin $B_1$, Vitamin $B_2$, pantothenic acid and related compounds. Generally speaking, since pantothenic acid is one of the water soluble Vitamin B group and its physioligical effect is compatible with that of coenzyme A (CoA) which is biosynthesized from pantothenic acid, an intermediary product in the biosynthetic pathway of coenzyme A can be used and illustrative of these are pantothenic acid, β-alanine, pantotheine, pantothine, aspartic acid, valine, dimethyl pyruvate, α-keto-pantoic acid, pantothenyl cysteine, D(+)-4-phospho pantotheine, dephospho coenzyme A, coenzyme A and the like. The derivatives of those compounds (e.g., carnosine or anserine containing β-alanine therein) and natural substances containing those compounds (e.g., yeast extract, corn steep liquor, fish soluble, meat extract, rice bran, molasses, powdered liver, peptone, NZ-amine, distillers' soluble and the like) can be also used.

Thiamine-related substances such as 4-amino-5-aminomethyl-2-methylpyrimidine, 4-methyl-5-β-hydroxyethylthiazole and the like can be used as a substitute for Vitamin $B_1$. The natural substances containing those compounds can be also used.

The accumulation of CAMP can be increased by adding in advance or in the course of culturing to the medium an inhibitor of cyclic-3',5'-nucleotidephosphodiesterase such as, for example, methylxanthines such as caffeine, theophylline, theobromine or the like, 2,3-, 2,4- or 2,5-pyridinedicarboxylic acid, dipicolinic acid, 8-hydroxyquinoline, polyphosphoric acid, pyrophosphoric acid and the like in the rate of 0.001–500 mg/l.

The production of CAMP can be further increased by adding the foregoing precursors to the medium in some cases of the present invention.

For example, when precursor is added to a culture medium containing a microorganism of the strains Corynebacterium murisepticum No. 7-10 (ATCC 21977, FERM-P No. 1555), Arthrobacter 11-211 (ATCC 21978, FERM-P No. 1556), Microbacterium No. 205-CM7 (ATCC 21979, FERM-P No. 1557), Microbacterium No. 205-CM-XA3 (ATCC 21980, FERM-P No. 1558) and Microbacterium No. 205-MP-197 (ATCC 21976, FERM-P No. 2449) or the like, the production of CAMP is further increased.

The culturing may be carried out by any appropriate method, e.g., with shaking, with agitation, with aeration or the like.

When the accumulation of CAMP attains its maximum, the culture is stopped, and then CAMP is isolated and purified. In the isolation and purification thereof, a means such as treatment with active carbon, treatment with a cationic or anionic exchange resin, addition of CAMP-insoluble solvent may be properly employed in combination. For example, CAMP contained in the cultured broth from which the fungal bodies have been removed is adsorbed on an active carbon, and the adsorbed CAMP is eluted with ammoniac aqueous alcohol solution, ammoniac aqueous acetone solution or the like. After the excess ammonia is removed by subjecting the eluate to concentration under reduced pressure or the like, CAMP is adsorbed on an anionic exchange resin [e.g., Dowex I chloride form (Trade mark of Dow Chemical Co., Ltd., U.S.A.), Dowex I formate form or the like] and then the adsorbed CAMP is eluted with an appropriate solvent [e.g., with dilute hydrochloric acid or calcium chloride + dilute hydrochloric acid system for Dowex I (chloride form) or with dilute formic acid or dilute formic acid + sodium formate system for Dowex I (formate form)]. CAMP in the eluate is again adsorbed on an active carbon and the adsorbed CAMP is eluted with ammoniac aqueous alcohol solution, ammoniac aqueous acetone solution or the like. Thereafter, the excess ammonia is removed by subjecting the eluate to concentration under a reduced pressure and CAMP is adsorbed on a cationic exchange resin [e.g., Dowex 50 ($H^+$ form)]. The adsorbed CAMP is eluted with dilute hydrochloric acid. CAMP can be separated in the form of crystal by concentrating the thus obtained eluate under reduced pressure and leaving the resultant in a cold chamber or adding CAMP-insoluble solvent such as alcohol, acetone or the like to the eluate.

For another method, CAMP in the fungal body-free cultured broth is adsorbed on an active carbon and the adsorbed CAMP is eluted with ammoniac aqueous alcohol solution, ammoniac aqueous acetone solution or the like. Thereafter, the excess ammonia is removed by subjecting the eluate to concentration under reduced pressure or the like and an organic solvent is added to the resultant under acidic condition with hydrochloric acid to obtain crude crystals of CAMP. The crude crystals may be purified with the foregoing anionic exchange resin or cationic exchange resin. The purified crystalline CAMP may be also obtained by dissolving the crude crystals to water, decoloring the resultant using a decolorizing resin [e.g., Duolite S-30 (Trade Mark of Chemical Process Co., Ltd., U.S.A.)] under acidic condition with hydrochloric or sulfuric acid and adding a CAMP-insoluble solvent such as alcohol, acetone or the like to the decolorized solution. The crystal of CAMP may be obtained by adsorbing CAMP in the fungal body-free cultured broth directly on an anionic or cationic exchange resin, subjecting the eluate to active carbon treatment and purification with a decolorizing resin and adding CAMP-insoluble solvent to the resultant.

The product as produced according to the present process coincides with the authentic CAMP in results of elementary analysis, assays of ribose and phosphorus, ultraviolet absorption and infrared absorption spectra.

The following examples are given to illustrate the present invention but are not to be considered a limitation thereupon.

EXAMPLE 1

Microbacterium No. 205-CM7 (ATCC 21979, FERM-P No. 1557) was precultured in a slant culture medium composed of 0.5% of $(NH_4)_2SO_4$, 0.5% of $KH_2PO_4$, 0.05% of $MgSO_4.7H_2O$, 1% of casamino acid, 0.3% of yeast extract, 1% of glucose, 2% of agar and of pH 7.0 (adjusted with 3N KOH aqueous solution).

Separately, 30 ml each of a medium composed of 5% of glucose, 0.01% of $ZnSO_4.7H_2O$, 0.5% of urea, 0.5% of $(NH_4)_2SO_4$, 1% of $KH_2PO_4$, 1% of $K_2HPO_4$, 0.5% of arginine, 30 γ/l of biotin, 1% of $MgSO_4.7H_2O$ and of pH 7.5 (adjusted with 3N KOH aqueous solution) was poured into a 500 ml flask for shaking culture and subjected to sterilization at 115° C for 10 minutes using an autoclave. The obtained seed culture was inoculated in said medium and cultured with shaking at 30° C for 48 hours. As a result, 1.0 mg/ml of CAMP was accumulated in the medium.

The cultured broth was centrifuged to remove the fungal bodies and the supernatant of the broth adjusted to pH 4 with 3N HCl aqueous solution was adsorbed on an active carbon. The adsorbed CAMP was eluted with ethyl alcohol containing 0.7% of ammonia and the eluate was concentrated under reduced pressure to remove excess ammonia, and then adjusted to pH 8.0 with ammonia. The resultant eluate was passed through a column packed with Dowex I formate form having a mesh of 100–200 to adsorb CAMP. Subsequently, the column was washed with 0.02 N formic acid solution and the adsorbed CAMP was eluted with 0.15 N formic acid solution. The eluate was again adsorbed on an active carbon and the adsorbed CAMP was eluted with 0.7% ammonia-containing ethyl alcohol. The eluate was concentrated under reduced pressure and adjusted to pH 2.0 with hydrochloric acid. The resultant eluate was passed through a column packed with Dowex 50 hydrogen form having a mesh of 100–200 to adsorb CAMP and the adsorbed CAMP was eluted with 0.05 N HCl aqueous solution. The eluate was again concentrated under reduced pressure and left in a cold chamber (2°–3° C) to obtain 600 mg of CAMP crystals out of 1000 ml of the cultured broth.

The parent strain of the present mutant, Microbacterium No. 205 (ATCC 21376, FERM-P No. 106) was cultured in the same manner as described above, but CAMP was hardly accumulated in the cultured broth.

EXAMPLE 2

Corynebactericum murisepticum No. 7 - 10 (ATCC 21977, FERM-P No. 1555) was precultured in a slant culture medium composed of 1% of beef extract, 1% of polypeptone, 0.5% of yeast extract, 0.3% of sodium chloride, 2% of agar and whose pH was adjusted to 7.0 with 3N KOH aqueous solution.

Separately, 60 ml each of a medium composed of 5% of glucose, 0.5% of urea, 0.5% of ammonium sulfate, 1% of $KH_2PO_4$, 1% of $K_2HPO_4$, 1% of polypeptone, 0.5% of yeast extract, 1% of $MgSO_4.7H_2O$, 0.01% of $ZnSO_4.7H_2O$ and whose pH was adjusted to 7.5 with 3N KOH aqueous solution was poured into a 500 ml flask for shaking culture and subjected to sterilization at 115° C for 10 minutes using an autoclave. The obtained seed culture was inoculated in said medium and cultured at 30° C for 72 hours with shaking at the rate of 140 r.p.m. As a result, 1.2 mg/ml of CAMP was accumulated in the medium.

After the culture is centrifuged to remove fungal bodies, the supernatant was treated in the same manner as described in Example 1 to obtain 610 mg of CAMP crystals out of 1000 ml of the cultured broth. The parent strain of the present mutant, Corynebacterium murisepticum No. 7 (ATCC 21374, FERM-P No. 206) was cultured in the same manner as described above, but CAMP was hardly accumulated in the cultured broth.

EXAMPLE 3

Arthrobacter 11 - 211 (ATCC 21978, FERM-P No. 1556) was precultured in the same medium as employed in Example 2 at 30° C for 24 hours and the obtained seed culture was inoculated in 100 ml each of a medium in a 500 ml flask for shaking culture; said medium composed of 5% of glucose, 0.5% of ammonium sulfate, 1% of $K_2HPO_4$, 0.5% of urea, 0.5% of $KH_2PO_4$, 1% of polypeptone, 1% of $MgSO_4 \cdot 7H_2O$, 0.5% of yeast extract, 0.01% of $ZnSO_4 \cdot 7H_2O$, 0.0005% of $FeSO_4 \cdot 7H_2O$ and of pH 7.0 (adjusted with a KOH aqueous solution) was poured into a 500 ml flask for shaking culture at the rate of 100 ml per flask, respectively, and sterilized at 115° C for 10 minutes using an autoclave. The inoculated medium was kept for culturing at 30° C for 48 hours with shaking. As a result, 1.3 mg/ml of CAMP was accumulated therein.

The cultured broth was centrifuged to remove fungal bodies and the resultant supernatant was treated in the same manner as described in Example 1 and 490 mg of CAMP crystals were obtained out of 1000 ml of the cultured broth. The parent strain of the present mutant, Arthrobacter 11 (ATCC 21375, FERM-P No. 207) was cultured in the same manner as described above, but CAMP was hardly accumulated in the cultured broth.

EXAMPLE 4

The culturing method described in Example 2 was followed, but substituting Microbacterium No. 205-CM7 (ATCC 21979, FERM-P No. 1557) for *Corynebacterium murisepticum* No. 7-10 (ATCC 21977, FERM-P No. 1555) to give 2.8 mg/ml of CAMP.

The cultured broth was centrifuged to remove fungal bodies and the supernatant was treated in the same manner as described in Example 1 to give 1.3 g of CAMP crystals out of 1000 ml of the cultured broth. The parent strain thereof, Microbacterium No. 205 (ATCC 21376, FERM-P No. 106) was cultured in the same manner as described above, but CAMP was hardly accumulated in the cultured medium.

EXAMPLE 5

Microbacterium No. 205-CM-XA3 (ATCC 21980, FERM-P No. 1558) was precultured in a slant culture medium composed of 0.5% of $(NH_4)_2SO_4$, 0.5% of $KH_2PO_4$, 0.05% of $MgSO_4 \cdot 7H_2O$, 1% of casamino acid, 1% of glucose, 0.01% of xanthine, 2% of agar and of pH 7.0. The obtained seed culture was inoculated in 30 ml each of a medium in a 500 ml flask for shaking culture; said medium composed of 5% of glucose, 0.5% of $(NH_4)_2SO_4$, 0.5% of urea, 1% of $KH_2PO_4$, 1% of $K_2HPO_4$, 1.5% of polypeptone, 1% of $MgSO_4 \cdot 7H_2O$, 0.5% of yeast extract, 100 γ/ml of xanthine, 0.01% of $ZnSO_4 \cdot 7H_2O$ and of pH 7.5 (adjusted with 3N-KOH aqueous solution) was poured into a 500 ml flask for shaking culture at the rate of 30 ml per flask, respectively, sterilized at 115° C for 10 minutes using an autoclave and added thereto 2% of calcium carbonate which was separately sterilized. The inoculated medium was kept for culturing at 30° C for 70 hours with shaking to give 6.7 mg/ml of CAMP.

The cultured broth was centrifuged to remove fungal bodies and the supernatant was treated in the same manner as described in Example 1. As a result, 3.1 g of CAMP crystals was obtained out of 1000 ml of the cultured broth. The parent strain of the present mutant, Microbacterium No. 205 (ATCC 21376, FERM-P No. 106) was cultured in the same manner as described above, but CAMP was hardly accumulated in the cultured broth.

EXAMPLE 6

Microbacterium No. 205-CM7 (ATCC 21979, FERM-P No. 1557) was precultured in a slant culture medium composed of 0.5% of $(NH_4)_2SO_4$, 0.5% of $KH_2PO_4$, 0.05% of $MgSO_4 \cdot 7H_2O$, 1% of casamino acid, 0.3% of yeast extract, 1% of glucose, 2% of agar and of pH 7.0 (adjusted with 3N-KOH aqueous solution). The obtained seed culture was inoculated in 30 ml each of a medium in a 500 ml flask for shaking culture; said medium composed of 5% of glucose, 0.01% of $ZnSO_4 \cdot 7H_2O$, 0.5% of urea, 0.5% of $(NH_4)_2SO_4$, 1% of $KH_2PO_4$, 1% of $K_2HPO_4$, 0.2% of glycine, 1 mg/l of biotin, 100 mg/l of calcium pantothate, 10 mg/l of thiamine hydrochloride, 1% of $MgSO_4 \cdot 7H_2O$, 0.4% of one of the precursors listed in Table 4 and of pH 7.5 (adjusted with 3N-KOH aqueous solution) was poured into a 500 ml flask for shaking culture at the rate of 30 ml per flask, respectively, and sterilized at 115° C for 10 minutes using an autoclave. The culturing was conducted at 30° C for 48 hours with shaking to accumulate CAMP.

The cultured broth was centrifuged to remove fungal bodies and the supernatant was treated in the same manner as described in Example 1 to give crystals of CAMP. The results obtained are shown in Table 4. As a reference, the culturing was conducted in the same manner as described above except that any of precursors was not added to the culture medium.

Table 4

| Precursor | Accumulated CAMP (mg/ml) | CAMP crystals (g/l) |
|---|---|---|
| Adenine | 2.5 | 0.74 |
| Adenosine | 4.5 | 1.34 |
| 5'-Adenylic acid | 4.8 | 1.42 |
| 3'-Adenylic acid | 2.0 | 0.67 |
| Hypoxanthine | 5.0 | 1.60 |
| Inosine | 5.3 | 1.63 |
| 5'-Inosinic acid | 5.2 | 1.60 |
| 3'-Inosinic acid | 2.1 | 0.68 |
| 5-Amino-4-imidazole-carboxamide | 4.5 | 1.24 |
| 5-Amino-4-imidazole-carboxamide riboside | 4.8 | 1.35 |
| Reference (Control: no precursor) | 1.5 | 0.60 |

The parent strain of the present mutant, Microbacterium No. 205 (ATCC 21376, FERM-P No. 106) was cultured in the same manner as described above except that any of precursors was not added to the culture medium, but CAMP was hardly accumulated in the cultured broth.

EXAMPLE 7

Microbacterium No. 205-MP-197 (ATCC 21976, FERM-P No. 2449) was cultured in the same manner as described in Example 1 and 3.5 mg/ml of CAMP were accumulated. The cultured broth was centrifuged to remove fungal bodies. The supernatant was treated in the same manner as described in Example 1 to give 1.22 g of CAMP crystal out of 1000 ml of the cultured broth. The parent strain of the present mutant, Microbacterium No. 205 (ATCC 21376, FERM-P No. 106) was cultured in the same manner as described above, but CAMP was hardly accumulated in the cultured broth.

What is claimed is:

1. A process for producing 3', 5'-cyclic adenylic acid which comprises culturing under aerobic conditions a strain of microorganism, capable of producing 3', 5'-cyclic adenylic acid without using a precursor thereof and in the absence of fluoride, said microorganism being selected from the group consisting of microorganisms belonging to the genera Corynebacterium, Arthrobacter and Microbacterium, in a medium containing carbon and nitrogen sources, inorganic nutrient substances and no precursor at pH 5-9, at a temperature of 20° – 40° C until 3', 5'-cyclic adenylic acid is accumulated in the medium, and recovering 3', 5'-cyclic adenylic acid from the medium.

2. A process according to claim 1, wherein the microorgansim is one member selected from the group consisting of microorganisms belonging to the species of *Corynebacterium murisepticum*, Arthrobacter 11 and Microbacterium No. 205.

3. A process according to claim 1, wherein said strain of microorganism is one member selected from the group consisting of *Corynebacterium murisepticum* No. 7 - 10 (ATCC 21977, FERM-P No. 1555), Arthrobacter 11 - 211 (ATCC 21978, FERM-P No. 1556), Microbacterium No. 205 - CM7 (ATCC 21979, FERM-P No. 1557), microbacterum No. 205-CM-XA3 (ATCC 21980, FERM-P No. 1558), and Microbacterium No. 205-MP-197 (ATCC 21976, FERM-P No. 2449).

4. A process according to claim 1, wherein the culture is conducted with shaking agitation or aeration.

5. A process according to claim 1, wherein the culture is carried out for 24 to 80 hours.

6. A process according to claim 1, wherein the recovering is conducted by treating the medium in which the 3', 5'-cyclic adenylic acid is accumulated with at least one recovery technique selected from the group consisting of active carbon, anionic ion exchange resin, cationic ion exchange resin, decoloring resin, vacuum concentration and solvent incapable of dissolving the desired 3', 5'-cyclic adenylic acid.

7. A process according to claim 1, wherein the culture is conducted in the presence of a small amount of at least one member selected from the group consisting of biotin, vitamin $B_1$, vitamin $B_2$, pantothenic acid.

8. A process according to claim 1, wherein the culture is conducted in the presence of 0.001-500 mg per liter of an inhibitor of cyclic 3', 5'-nucleotide-phosphodiesterase selected from the group consisting of caffein, theophilline, theobromine, 2, 3-2, 4-, and 2,5-pyridine dicarboxylic acid, dipicolinic acid, 8-hydroxyquinoline, polyphosphoric acid and pyrophosphoric acid, said inhibitor being added to the medium before or during the culture.

9. In the process of producing 3', 5'-cyclic adenylic acid which comprises culturing under aerobic conditions a strain of microorganism belonging to a species selected from the group consisting of Corynebacterium murisepticum, Arthrobacter 11 and Microbacterium No. 205 in a medium containing carbon and nitrogen sources, inorganic nutrient substances and a precursor selected from the group consisting of adenine, hypoxanthine succinyladenine, 5-amino-4-imidazolecarboxamide, 7-amino-pyrarolo-(4, 3-d)-pyramidine, pyrazolo-(4, 3-d)-pyramidine, 4-amino-pyrrolo-(4, 3-d)-pyrimidine, pyrrolo-(2, 3-d)-pyrimidine, a riboside containing one of the said compounds as a base or a monoribonucleotide thereof, at pH 5-9 at a temperature of 20°–40° C. until 3', 5'-cyclic adenylic acid is accumulated in the medium, and recovering 3', 5'-cyclic adenylic acid from the medium, the improvement comprising using as the microorganism one member selected from the group consisting of *Corynebacterium murisepticum* No. 7-10 (ATCC 21977, FERM-P No. 1555), Arthrobacter 11-211 (ATCC 21978, FERM-P No. 1556), Microbacterium No. 205-CM7 (ATCC 21979, FERM-P No. 1557), Microbacterium No. 205-CM-XA3 (ATCC 21980, FERM-P No. 1558), and Microbacterium No. 205-MP-197 (ATCC 21976, FERM-P No. 2449).

* * * * *